United States Patent
Bennett et al.

(10) Patent No.: US 6,210,892 B1
(45) Date of Patent: Apr. 3, 2001

(54) ALTERATION OF CELLULAR BEHAVIOR BY ANTISENSE MODULATION OF MRNA PROCESSING

(75) Inventors: C. Frank Bennett; Stanley T. Cooke; Muthiah Manoharan, all of Carlsbad; Jacqueline R. Wyatt, Encinitas; Brenda F. Baker, Carlsbad; Brett P. Monia, LaCosta; Susan M. Freier; Robert McKay, both of San Diego; James G. Karras, San Marcos, all of CA (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 09/277,020

(22) Filed: Mar. 26, 1999

Related U.S. Application Data

(63) Continuation-in-part of application No. 09/167,921, filed on Oct. 7, 1998.
(51) Int. Cl.$^7$ .............................. C12Q 1/68; C12P 19/34; C07H 21/04; C12N 5/00
(52) U.S. Cl. ............................ 435/6; 435/91.1; 435/375; 536/23.1; 536/24.3; 536/24.5
(58) Field of Search ............................ 536/24.5, 23.1; 435/6, 325, 375, 91.1, 91.31; 514/44

(56) References Cited

U.S. PATENT DOCUMENTS

| | | | |
|---|---|---|---|
| 5,627,274 | 5/1997 | Kole et al. | 536/23.1 |
| 5,776,905 | * 7/1998 | Gibbons et al. | 514/44 |

FOREIGN PATENT DOCUMENTS

| | | |
|---|---|---|
| WO 9304701 | * 3/1993 | (WO). |
| WO 94/26887 | 11/1994 | (WO). |
| WO 9640266 | * 12/1996 | (WO). |

OTHER PUBLICATIONS

Andrea D. Branch, A good antisense molecule is hard to find, TIBS, 47–48, Feb. 1998.*

Stanley T. Crooke, Basic Principles of Anitsense Therapeutics, Springer–Verlag, NY, p. 3, Jul. 1998.*

Rakesh Datta, et al., Overepression of Bcl–xL by Cytotoxic Drug Exposure Confers resistance to ionizing radiation–induced Internucleosomal DNA Fragmentation. Cell Growth & Differentiation vol. 6, pp. 363–370, Apr. 1995.*

Chu, et al., "Alternatively Processed Human E–Selecting Transcripts Linked to Chronic Expression of E–Selecting In Vivo", *J. Immunol.*, 1994, 153, 4179–4189.

Hodges, D., "Inhibition of Splicing of Wild–Type and Mutated Luciferase–Adenovirus Pre–mRNAs by Antisense Oligonucleotides", *Mol. Pharmacol.*, 1995, 48, 905–918.

Dominski, et al., "Restoration of correct splicing in thalassemic pre–mRNA by antisense oligonucleotides", Proc.Natl.Acad.Sci.USA, 1993, 90, 8673–8677.

Dunckley, et al., "Modification of Splicing in the dystrophin gene in cultured Mdx muscle cells by antisense oligoribonucleotides", *Human Mol.Genetics*, 1998, 5, 1083–90.

Dunckley, et al., "Modulation of Splicing in the DMD Gene by Antisense Oligoribonucleotides", *Nucleosides & Nucleosides*, 1997, 16, 1665–1668.

Klasens et al., "Inhibition of polyadenylation by stable RNA secondary structure", *Nuc.Acids Res.*, 1998 26, 1870–1876.

Kole R., "Modification of pre–mRNA splicing by antisense oligonucleotides", *Acta Biochimica Polonica*, 1997, 44, 231–238.

Moulds, C., et al., "Site and Mechanism of Antisense Inhibition of C–5 Propyne Oligonucleotides", *Biochem.* 1995 34, 5044–53.

Sierakowska, et al., "Repair of thalassemic human β–globin in mRNA in mammalian cells by antisense oligonucleotides", *Proc.Natl.Acad.Sci.USA*, 1996 93, 12840–44.

Sierakowska, H., "Restoration of β–Globin Gene Expression in Mammalian Cells by Antisense Oligonucleotides that Modify the Aberrant Splicing Patterns of Thalassemic Pre–mRNAs", *Nucleosides & Nucleotides*, 1997, 16, 1173–1182.

Takeshima, et al., "Modulation of in Vitro Splicing of the Upstream Intron by Modifying an Intra–Exon Sequence Which Is Deleted from the Dystrophin Gene in Dystrophin Kobe", *J. Clin. Invest.* 1995 95, 515–520.

Tuypens, et al., "Organization and chromosomal localization of the human interleukin 5 receptor α–chain gene", *Eur. Cytokine Netw.*, 1992 3, 451–459.

Wang, et al., "Antisense Oligodeoxynucleotdes Selectively Suppress Expression of the Mutant α2 (1) Collagen Allele in Type IV Osteogenesis Imperfecta Fibroblasts", *J. Clin Invest.*, 1996, 97, 448–454.

* cited by examiner

Primary Examiner—Robert A. Schwartzman
Assistant Examiner—Janet Epps
(74) Attorney, Agent, or Firm—Law Offices of Jane Massey Licata

(57) ABSTRACT

The present invention provides compositions and methods for controlling the behavior of a cell, tissue or organism through antisense modulation of mRNA processing, using antisense compounds which does not support cleavage of the mRNA target.

31 Claims, No Drawings

ALTERATION OF CELLULAR BEHAVIOR BY ANTISENSE MODULATION OF MRNA PROCESSING

This application is a continuation-in-part of U.S. application Ser. No. 09/167,921 filed Oct. 7, 1998.

FIELD OF THE INVENTION

The present invention provides compositions and methods for controlling a cellular behavior by antisense modulation of messenger RNA (mRNA)processing. In particular, this invention relates to antisense compounds, particularly oligonucleotides, which modulate RNA splicing, polyadenylation, or stability in order to affect the behavior of a cell.

BACKGROUND OF THE INVENTION

Newly synthesized eukaryotic mRNA molecules, known as primary transcripts or pre-mRNA, made in the nucleus, are processed before or during transport to the cytoplasm for translation. A methylated cap structure, consisting of a terminal nucleotide, 7-methylguanylate, is added to the 5' end of the mRNA in a 5'—5' linkage with the first nucleotide of the mRNA sequence.

An approximately 200–250-base sequence of adenylate residues, referred to as poly(A), is added posttranscriptionally to a site that will become the 3' terminus of the mRNA, before entry of the mRNA into the cytoplasm. This is a multistep process which involves assembly of a processing complex, then site-specific endonucleolytic cleavage of the precursor transcript, and addition of a poly(A) "tail." In most mRNAs the polyadenylation signal sequence is a hexamer, AAUAAA, located 10 to 30 nucleotides in the 5' direction (upstream) from the site of cleavage (5'-CA-3') in combination with a U or G-U rich element 3' to the cleavage site. Multiple poly(A) sites may be present on a given transcript, of which only one is used per transcript, but more than one species of mature mRNA transcript can be produced from a given pre-mRNA via use of different poly(A) sites. It has recently been shown that stable mRNA secondary structure can affect the site of polyadenylation of an RNA construct in transfected cells. Klasens et al., *Nuc. Acids Res.*, 1998, 26, 1870–1876. It has also been found that which of multiple polyadenylation sites is used can affect transcript stability. Chu et al., *J. Immunol.*, 1994, 153, 4179–4189. Antisense modulation of mRNA polyadenylation has not previously been reported.

The next step in mRNA processing is splicing of the mRNA, which occurs in the maturation of 90–95% of mammalian mRNAs. Introns (or intervening sequences) are regions of a primary transcript (or the DNA encoding it) that are not included in a finished mRNA. Exons are regions of a primary transcript that remain in the mature mRNA when it reaches the cytoplasm. The exons are "spliced" together to form the mature mRNA sequence. Intron-exon junctions are also referred to as "splice sites" with the 5' side of the junction often called the "5' splice site," or "splice donor site" and the 3' side the "3' splice site" or "splice acceptor site." "Cryptic" splice sites are those which are less often used but may be used when the "usual" splice site is blocked or unavailable." Alternative splicing, i.e., the use of various combinations of exons, often results in multiple mRNA transcripts from a single gene.

A final step in RNA processing is turnover or degradation of the mRNA. Differential mRNA stabilization is one of several factors in the rate of synthesis of any protein. mRNA degradation rates seem to be related to presence or absence of poly(A) tails and also to the presence of certain sequences in the 3' end of the mRNA. For example, many mRNAs with short half-lives contain several $A(U)_nA$ sequences in their 3'-untranslated regions. When a series of AUUUA sequences was inserted into a gene not normally containing them, the half life of the resulting mRNA decreased by 80%. Shaw and Kamen, *Cell*, 1986, 46, 659. This may be related to an increase of nucleolytic attack in sequences containing these $A(U)_nA$ sequences. Other mediators of mRNA stability are also known, such as hormones, translation products (autoregulation/feedback), and low-molecular weight ligands.

Antisense compounds have generally been used to interfere with protein expression, either by interfering directly with translation of the target molecule or, more often, by RNAse-H-mediated degradation of the target mRNA. Antisense interference with 5' capping of mRNA and prevention of translation factor binding to the mRNA by oligonucleotide masking of the 5' cap have been disclosed by Baker et al. (WO 91/17755).

Antisense oligonucleotides have been used to modulate splicing, particularly aberrant splicing or splicing of mutant transcripts, often in cell-free reporter systems. A luciferase reporter plasmid system has been used to test the ability of antisense oligonucleotides targeted to the 5' splice site, 3' splice site or branchpoint to inhibit splicing of mutated or wild-type adenovirus pre-mRNA sequences in a reporter plasmid. Phosphorothioate oligodeoxynucleotides that can support RNAse H cleavage were found to be better inhibitors of expression of the wild-type adenovirus construct than the 2'-methoxy phosphorothioates that cannot support RNase H, although the reverse was true for oligonucleotides targeted to an adenovirus construct containing human β-globin splice site sequences. Hodges and Crooke, *Mol. Pharmacol.*, 1995, 48, 905–918.

Antisense oligonucleotides have been used to target mutations that lead to aberrant splicing in several genetic diseases. Use of antisense compounds to correct aberrant processing of mutated mRNA sequences is not comprehended by the present invention. Altering, i.e., controlling, the behavior of a cell, particularly the response of a cell to a stimulus, by antisense modulation of "wild-type" or native mRNA processing, the subject of the present invention, has not been described previously.

Phosphorothioate 2'-O-methyl oligoribonucleotides, have been used to target the aberrant 5' splice site of the mutant β-globin gene found in patients with β-thalassemia, a genetic blood disorder. Aberrant splicing of mutant β-globin mRNA was blocked in vitro in vector constructs containing thalassemic human β-globin pre-mRNAs using 2'-O-methyl-ribo-oligonucleotides targeted to the branch point sequence in the first intron of the mutant human β-globin pre mRNAs. 2'-O-methyl oligonucleotides are used because they are stable to RNAses and form stable hybrids with RNA that are not degraded by RNAse H. Dominski and Kole, *Proc. Natl. Acad. Sci.* USA, 1993, 90, 8673–8677. A review article by Kole discusses use of antisense oligonucleotides targeted to aberrant splice sites created by genetic mutations such as β-thalassemia or cystic fibrosis. It was hypothesized that blocking a splice site with an antisense oligonucleotide will have similar effect to mutation of the splice site, i.e., redirection of splicing. Kole, *Acta Biochimica Polonica*, 1997, 44, 231–238. Oligonucleotides targeted to the aberrant β-globin splice site suppressed aberrant splicing and at least partially restored correct splicing in HeLa cells expressing the mutant transcript. Sierakowska et al., Nucleosides &

Nucleotides, 1997, 16,1173–1182; Sierakowska et al., *Proc. Natl. Acad. Sci. USA*, 1996, 93, 12840–44. U.S. Pat. No. 5,627,274 discloses and WO 94/26887 discloses and claims compositions and methods for combating aberrant splicing in a pre-mRNA molecule containing a mutation, using antisense oligonucleotides which do not activate RNAse H.

Modulation of mutant dystrophin splicing with 2'-O-methyl oligoribonucleotides has been reported both in vitro and in vivo. In dystrophin Kobe, a 52-base pair deletion mutation causes exon 19 to be skipped during splicing. An in vitro minigene splicing system was used to show that a 31-mer 2'-O-methyl oligoribonucleotide complementary to the 5' half of the deleted sequence in dystrophin Kobe exon 19 inhibited splicing of wild-type pre-mRNA. Takeshima et al., *J. Clin. Invest.*, 1995, 95, 515–520. The same oligonucleotide was used to induce exon skipping from the native dystrophin gene transcript in human cultured lymphoblastoid cells.

Dunckley et al., (*Nucleosides & Nucleotides*, 1997, 16, 1665–1668) describes in vitro constructs for analysis of splicing around exon 23 of mutated dystrophin in the mdx mouse mutant, a model for Duchenne muscular dystrophy. Plans to analyze these constructs in vitro using 2' modified oligos targeted to splice sites within and adjacent to mouse dystrophin exon 23 are discussed, though no target sites or sequences are given.

2'-O-methyl oligoribonucleotides were subsequently used to correct dystrophin deficiency in myoblasts from the mdx mouse. An antisense oligonucleotide targeted to the 3' splice site of murine dystrophin intron 22 caused skipping of the mutant exon and created a novel in-frame dystrophin transcript with a novel internal deletion. This mutated dystrophin was expressed in 1–2% of antisense treated mdx myotubes. Use of other oligonucleotide modifications such as 2'-O-methoxyethyl phosphodiesters are disclosed. Dunckley et al. (*Human Mol. Genetics*, 1998, 5, 1083–90).

Phosphorothioate oligodeoxynucleotides have been used to selectively suppress the expression of a mutant α2(I) collagen allele in fibroblasts from a patient with osteogenesis imperfecta, in which a point mutation in the splice donor site produces mRNA with exon 16 deleted. The oligonucleotides were targeted either to the point mutation in the pre-mRNA or to the defectively spliced transcript. In both cases mutant mRNA was decreased by half but the normal transcript is also decreased by 20%. This was concluded to be fully accounted for by an RNAse H-dependent mechanism. Wang and Marini, *J. Clin Invest.*, 1996, 97, 448–454.

A microinjection assay was used to test the antisense effects on SV40 large T antigen (TAg) expression of oligonucleotides containing C-5 propynylpyrimidines, either as 2'-O-allyl phosphodiester oligonucleotides, which do not elicit RNAse H cleavage of the target, or as 2'-deoxy phosphorothioates, which do elicit RNAse H cleavage. Oligonucleotides targeted to the 5' untranslated region, translation initiation site, 5' splice junction or polyadenylation signal of the TAg transcript were injected into the nucleus or cytoplasm of cultured cells. The only 2'-O-allyl (non-RNAse H) oligonucleotides which were effective at inhibiting T-antigen were those targeted to the 5' untranslated region and the 5' splice junction. The 2'-O-allyl phosphodiester/C-5 propynylpyrimidine oligonucleotides, which do not elicit RNAse H, were 20 fold less potent than the oligodeoxynucleotides which had the ability to recruit RNAse H. The authors concluded that the duplexes formed between the RNA target and the 2'-O-allyl phosphodiester/C-5 propynylpyrimidine oligonucleotides dissociate rapidly in cells. Moulds et al., 1995, *Biochem.*, 34, 5044–53. Biotinylated 2'-O-allyloligoribonucleotides incorporating 2-aminoadenine bases were targeted to the U2 small nuclear RNA (snRNA), a component of the spliceosome, in HeLa nuclear extracts. These inhibited mRNA production with a concomitant accumulation of splicing intermediates. The present invention is directed to antisense compounds targeted to mRNA.

Use of antisense compounds to block or regulate mRNA polyadenylation has not previously been described. Regulation of mRNA stability using antisense oligonucleotides targeted to RNA sequences involved in RNA turnover or degradation has also not been previously described.

There is, therefore a continued need for compositions and methods for altering the behavior of a cell, particularly the response of a cell to a stimulus, by modulation of normal mRNA processing. The present invention provides antisense compounds for such modulation. The compositions and methods of the invention can be used in therapeutics, including prophylaxis, and as research tools.

SUMMARY OF THE INVENTION

The present invention provides methods for controlling the behavior of a cell through modulation of the processing of a selected wild-type mRNA target within said cell, by binding to the mRNA target an antisense compound which is specifically hybridizable to the mRNA target and which does not support cleavage of the mRNA target upon binding. Compositions and therapeutic methods are also provided. In preferred embodiments, the mRNA processing may be splicing, polyadenylation or degradation of the mRNA. In some embodiments, the cellular behavior to be controlled may be apoptosis and/or the response of the cell to a stimulus.

DETAILED DESCRIPTION OF THE INVENTION

The present invention employs oligomeric antisense compounds, particularly oligonucleotides, for use in modulating the processing of mRNA within a cell, ultimately controlling the behavior of the cell, especially the response of the cell to an external or internal stimulus. Examples of cellular behaviors include mitosis, apoptosis or programmed cell death, quiescence, and differentiation. Examples of external stimuli are stress (including chemical stressors) hormones, cytokines and other signaling molecules.

Modulation of mRNA processing is accomplished by providing antisense compounds which specifically modulate one or more mRNA processing events, such as RNA splicing, polyadenylation, capping, and degradation. Data from a variety of molecular targets are provided as illustrations of the invention. As used herein, the terms "target nucleic acid" and "nucleic acid encoding a target" encompass DNA encoding a given molecular target (i.e., a protein or polypeptide), RNA (including pre-mRNA and mRNA) transcribed from such DNA, and also cDNA derived from such RNA. The specific hybridization of an antisense compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The overall effect of such interference with target nucleic acid function is modulation of the expression of the target molecule. In the context of the present invention, "modulation" means a quantitative change, either an increase (stimulation) or a decrease (inhibition), for example in the frequency of an RNA processing event or in the expression of a gene. In this context, modulation can also mean "redirection," for example redirection of splicing which results in an increase in one splice product of a target RNA and concomitant decrease in another splice product with no significant change in the total target RNA levels.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. The targeting process also includes determination of a site or sites within this gene for the antisense interaction to occur such that the desired effect, e.g., modulation of expression of RNA processing, will result. Within the context of the present invention, preferred target site(s) depend on the aspect of RNA processing to be modulated. For modulation of mRNA splicing, splice donor sites or splice acceptor sites, collectively also known as intron-exon junctions, are preferred target sites. Splicing branch points and exons (define) are also preferred target sites for modulation of mRNA splicing. For modulation of polyadenylation, a polyadenylation signal or polyadenylation site is a preferred target site. For modulation of mRNA stability or degradation, stabilizing or destabilizing sequences are preferred target sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. An antisense drug, Vitravene™, has been approved by the U.S. Food and Drug Administration for the treatment of cytomegalovirus retinitis (CMVR), a cause of blindness, in AIDS patients. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, acetamide, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a $O(CH_2)_2ON(CH_3)_2$ group, also known as 2'-DMAOE, and 2'-dimethylamino-ethoxyethoxy (2'-DMAEOE), i.e., 2'-O—$CH_2$—O—$CH_2$—N($CH_3$)$_2$.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'–5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941, and 5,750,692, each of which is herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), palmityl moiety (Mishra et al., *Biochim. Biophys. Acta*, 995, 1264, 229–237), or an octadecylamine or hexylamino-carbonyl-oxycholesterol moiety (Crooke et al., *J. Pharmacol. Exp. Ther.*, 1996, 277, 923–937).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids, gapped oligonucleotides or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety. Gapped oligonucleotides in which a region of 2'-deoxynucleotides, usually 5 contiguous nucleotides or more, often 10 contiguous deoxynucleotides, is present along with one or two regions of 2'-modified oligonucleotides are often used in antisense technology because uniformly 2'-modified oligonucleotides do not support RNAse H cleavage of the target RNA molecule. Enhanced binding affinity is provided by the 2' modifications and the deoxy gap region allows RNAse H cleavage of the target. However, in some situations such as modulation of RNA processing as described in the present invention, RNAse H cleavage of the target RNA is not desired. A functional RNA product, albeit with altered function, rather than an ablated RNA product is the goal of the present invention. The present invention, therefore, is limited to use of oligonucleotides that do not elicit cleavage, via RNAse H or otherwise, of the RNA target. Consequently, uniformly modified oligonucleotides, i.e., oligonucleotides modified identically at each nucleotide or nucleoside position, are preferred embodiments. A particularly preferred embodiment is an oligonucleotide which is uniformly modified at the 2' position of the nucleotide sugar, for example with a 2' MOE, 2' DMAOE, or 2' acetamide modification at each position, or a combination of these. Other preferred modifications are backbone modifications, including MMI, morpholino and PNA modifications, which may be uniform or may be alternated with other linkages, particularly phosphodiester or phosphorothioate linkages, as long as RNAse H cleavage is not supported.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules.

The compounds of the invention may be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfoic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the behavior of a cell can be treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding a selected mRNA target, enabling sandwich and other assays to easily be constructed to exploit this fact. Hybridization of the antisense oligonucleotides of the invention with a nucleic acid encoding the selected mRNA target can be detected by means known in the art. Such means may include conjugation of an enzyme to the oligonucleotide, radiolabelling of the oligonucleotide or any other suitable detection means. Kits using such detection means for detecting the level of target in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification, including chimeric molecules or molecules which may have a 2'-O-methoxyethyl modification of every nucleotide sugar, are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 $\mu$m in diameter. (Idson, in *Pharmaceutical Dosage Forms,* Lieberman, Rieger and Banker (Eds.), 1988, Marcel Dekker, Inc., New York, N.Y., volume 1, p. 199; Rosoff, in *Pharmaceutical Dosage Forms,* Lieberman, Rieger and Banker (Eds.), 1988, Marcel Dekker, Inc., New York, N.Y., Volume 1, p. 245; Block in *Pharmaceutical Dosage Forms,* Lieberman, Rieger and Banker (Eds.), 1988, Marcel Dekker, Inc., New York, N.Y., volume 2, p. 335; Higuchi et al., in *Remington's Pharmaceutical Sciences,* Mack Publishing Co., Easton, Pa., 1985, p. 301). Emulsions are often biphasic systems comprising of two immiscible liquid phases intimately mixed and dispersed with each other. In general, emulsions may be either water-in-oil (w/o) or of the oil-in-water (o/w) variety. When an aqueous phase is finely divided into and dispersed as minute droplets into a bulk oily phase the resulting composition is called a water-in-oil (w/o) emulsion. Alternatively, when an oily phase is finely divided into and dispersed as minute droplets into a bulk aqueous phase the resulting composition is called an oil-in-water (o/w) emulsion. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not.

Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms,* Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms,* Lieberman, Rieger and Banker (Eds.), 1988, Marcel Dekker, Inc., New York, N.Y., volume 1, p. 285; Idson, in *Pharmaceutical Dosage Forms,* Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms,*

Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms,* Lieberman, Rieger and Banker (Eds.), 1988, Marcel Dekker, Inc., New York, N.Y., volume 1, p. 335; Idson, in *Pharmaceutical Dosage Forms,* Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms,* Lieberman, Rieger and Banker (Eds.), 1988, Marcel Dekker, Inc., New York, N.Y., volume 1, p. 199). Emulsion formulations for oral delivery have been very widely used because of reasons of ease of formulation, efficacy from an absorption and bioavailability standpoint. (Rosoff, in *Pharmaceutical Dosage Forms,* Lieberman, Rieger and Banker (Eds.), 1988, Marcel Dekker, Inc., New York, N.Y., volume 1, p. 245; Idson, in *Pharmaceutical Dosage Forms,* Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms,* Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems,* Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences,* Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release,* 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting,* 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research,* 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such nonionic liposomal systems were effective in facilitating the deposition of cyclosporin-A into different layers of the skin (Hu et al. *S.T.P.Pharma. Sci.,* 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765). Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.,* 1980, 53, 2778) described liposomes comprising a nonionic detergent, $2C_{12}15G$, that contains a PEG moiety. Illum et al. (*FEBS Lett.,* 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.,* 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta,* 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.). Liposomes comprising PEG-modified ceramide lipids are described in WO 96/10391 (Choi et al.). U.S. Pat. No. 5,540,935 (Miyazaki et al.) and 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm.*

*Exp. Ther.,* 1992, 263, 25; Yamashita et al., *J. Pharm. Sci.,* 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems,* 1991, page 92; Muranishi, *Critical Reviews in Therapeutic Drug Carrier Systems,* 1990, 7, 1–33; Buur et al., *J. Control Rel.,* 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems,* 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems,* 1991, page 92); and non-steroidal anti-inflammatory agents such as diclofenac sodium, indomethacin and phenylbutazone (Yamashita et al., *J. Pharm. Pharmacol.,* 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.,* 1995, 5, 115–121; Takakura et al., *Antisense & Nucl. Acid Drug Dev.,* 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). See, generally, *The Merck Manual of Diagnosis and Therapy,* 15th Ed., Berkow et al., eds., 1987, Rahway, N.J., pages 1206–1228). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy,* 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, the standard cycle for unmodified oligonucleotides was utilized, except the wait step after pulse delivery of tetrazole and base was increased to 360 seconds.

Oligonucleotides containing 5-methyl-2'-deoxycytidine (5-Me—C) nucleotides were synthesized according to published methods [Sanghvi, et. al., *Nucleic Acids Research,* 1993, 21, 3197–3203] using commercially available phosphoramidites (Glen Research, Sterling Va. or ChemGenes, Needham Mass.).

2'-Fluoro amidites

2'-Fluorodeoxyadenosine amidites

2'-fluoro oligonucleotides were synthesized as described previously [Kawasaki, et. al., *J. Med. Chem.,* 1993, 36, 831–841] and U.S. Pat. No. 5,670,633, herein incorporated by reference. Briefly, the protected nucleoside N6-benzoyl-2'-deoxy-2'-fluoroadenosine was synthesized utilizing commercially available 9-beta-D-arabinofuranosyladenine as starting material and by modifying literature procedures whereby the 2'-alpha-fluoro atom is introduced by a $S_N2$-displacement of a 2'-beta-trityl group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies and standard methods were used to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate diisobutyryl-arabinofuranosylguanosine. Deprotection of the TPDS group was followed by protection of the hydroxyl group with THP to give diisobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites are prepared as follows, or alternatively, as per the methods of Martin, P., *Helvetica Chimica Acta*, 1995, 78, 486–504.

2,2'-Anhydro[1-(beta-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid that was crushed to a light tan powder (57 g, 85% crude yield). The NMR spectrum was consistent with the structure, contaminated with phenol as its sodium salt (ca. 5%). The material was used as is for further reactions (or it can be purified further by column chromatography using a gradient of methanol in ethyl acetate (10–25%) to give a white solid, mp 222–4° C.).

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product. Additional material was obtained by reworking impure fractions.

2'-O-Methoxyethyl-5'-O-dimethoxytrityl-5-methyluridine

2'O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/hexane/acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by TLC by first quenching the TLC sample with the addition of MeOH. Upon completion of the reaction, as judged by TLC, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/hexane(4:1). Pure product fractions were evaporated to yield 96 g (84%). An additional 1.5 g was recovered from later fractions.

3'-O-Acetyl-2'-O-methoxyethyl-5'-O-dimethoxytrityl-5-methyl-4-triazoleuridine

A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the latter solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methylcytidine

A solution of 3'-O-acetyl-2$^1$-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 mL) saturated with $NH_3$ gas was added and the vessel heated to 100° C. for 2 hours (TLC showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N4-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, TLC showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/hexane (1:1) containing 0.5% Et$_3$NH as the eluting solvent. The pure product fractions were evaporated to give 90 g (90%) of the title compound.

N4-Benzoyl-2'-O-methoxyethyl-5'-O-dimethoxytrityl-5-methylcytidine-3'-amidite N4-Benzoyl-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (TLC showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc/hexane (3:1) as the eluting solvent. The pure fractions were combined to give 90.6 g (87%) of the title compound.

2'-O-(Aminooxyethyl) nucleoside amidites and 2'-O-(dimethylaminooxyethyl) nucleoside amidites

2'-(Dimethylaminooxyethoxy) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenyl-chlorosilane (125.8 g, 119.0 mL, 1.1 leq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160 ° C. was reached and then maintained for 16 h (pressure <100 psig). The reaction vessel was cooled to ambient and opened. TLC (Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40–100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over P$_2$O$_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C. to 0° C. After 1 h the mixture was filtered, the filtrate was washed with ice cold CH$_2$Cl$_2$ and the combined organic phase was washed with water, brine and dried over anhydrous Na$_2$SO$_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5-methyluridine 5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10° C. under inert atmosphere. The reaction mixture was stirred for 10 minutes at 10° C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10° C. in an ice bath, sodium cyanoborohydride (0.39 g, 6.13 mmol) was added and reaction mixture stirred at 10° C. for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40° C. Then the reaction mixture was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl)guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

Example 2

Oligonucleotide Synthesis

Unsubstituted and substituted phosphodiester (P=O) oligonucleotides are synthesized on an automated DNA synthesizer (Applied Biosystems model 380B) using standard phosphoramidite chemistry with oxidation by iodine.

Phosphorothioates (P=S) are synthesized as for the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 h), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No 4,469,863, herein incorporated by reference.

3'-Deoxy-3'-methylene phosphonate oligonucleotides are prepared as described in U.S. Pat. No. 5,610,289 or U.S. Pat. No. 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Oligonucleotide Isolation

After cleavage from the controlled pore glass column (Applied Biosystems) and deblocking in concentrated ammonium hydroxide at 55° C. for 18 hours, the oligonucleotides or oligonucleosides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 6

Antisense Modulation of Polyadenylation

E-selectin, an adhesion molecule, is transiently expressed on endothelial cells in response to inflammatory cytokines and mediates adhesion of leukocytes. The human E-selectin genomic structure includes multiple AATAAA polyadenylation signals and a number of AUUUA transcript destabilizing elements with in the 3' untranslated region. It has been demonstrated that all three polyadenylation signals are functional, resulting in three types of E-selectin transcripts generated by differential use of these signals. The three transcripts (Type I, II and III) are differentially expressed in certain disease conditions. The Type I transcript lacks six of the transcript destabilizing elements, and has been shown to be more stable than the full-length Type III transcript. Chu et al., 1994, J. Immunol. 153:4179–4189.

The three AATAAA polyadenylation signals are located within the 3' untranslated sequence at nucleotides 2823, 2981 and 3816 according to the numbering scheme of Bevilacqua et al., 1989, Science 243, 1160–1165; GenBank Accession No. M24736. The actual polyadenylation sites are 13–20 bases downstream of each AATAAA signal.

Oligonucleotides 20 nucleobases in length were designed to target regions at and/or just downstream of each of these three polyadenylation sites. Oligonucleotides were made as uniformly 2'-methoxyethoxy (2'-MOE) compounds with either phosphorothioate (P=S) or phosphodiester (P=O) backbones.

The effects of these antisense compounds on polyadenylation and thus on transcript size and stability was measured. HUVEC (human umbilical vascular endothelial cells) are treated with antisense oligonucleotides targeted to E-selectin polyadenylation sites. Anchored-PCR amplification of human E-selectin mRNA 3' ends is performed according to Chu et al. (1994, J. Immunol. 153: 4179–4189) to determine which polyadenylation sites are still functional and in what amounts.

Direct measurements of the stability of the various transcripts present after oligonucleotide treatment can be performed using the rabbit reticulocyte lysate system described in Chu et al. (1994, J. Immunol. 153: 4179–4189).

Example 7

Antisense Modulation of Splicing in Mouse IL-5 Receptorα mRNA

The mRNA encoding the membrane form of the mouse IL-receptorα contains 11 exons. The transmembrane domain of the receptor is encoded in exon 9. Two mRNAs encoding soluble (secreted) forms of the receptor result from differential splicing events. The mRNA encoding soluble form 1 of the receptor is missing exon 9 (exon 8 is spliced to exon 10) and the mRNA encoding soluble form 2 is missing exons 9 and 10 (exon 8 is spliced to exon 11). Imamura et al., DNA and Cell Biology 13:283–292.

A series of antisense oligonucleotides were designed to "walk" the entire exon 9 of the coding region of murine IL-5 receptorα mRNA. Oligonucleotides were targeted to regions starting approximately every 10 nucleobases along the exon 9 sequence, which extends from nucleotides 1288 to 1381 on the sequence given as Genbank accession no. D90205, provided herein as SEQ ID NO: 9.

Murine $BCL_1$ cells were chosen for screening antisense oligonucleotides targeted to murine IL-5 receptorα. These are B-cell leukemia cells derived from a spontaneously arising tumor of BALB/c origin, and proliferate in response to murine or human IL-5. This is a CD5+ line which resembles a subset of human chronic lymphocytic leukemia tumors and secretes IgM upon lipopolysaccharide stimulation. Cells were obtained from the American Type Culture Collection and cultured in RPMI 1640 medium supplemented with 10% heat-inactivated fetal bovine serum (Sigma Chemical Co., St. Louis, Mo.), 10 mM Hepes, pH 7.2, 50 μM 2-ME, 2 mM L-glutamine, 100 U/ml penicillin and 100 μg/ml streptomycin (Gibco, Grand Island, N.Y.).

The effect of these compounds on both membrane and soluble forms of murine IL-5 receptorα were measured and are shown in Table 1. Oligonucleotides were screened in $BCL_1$ cells at a dose of 10 μM and IL-5 receptorα mRNA was measured by Northern blot. Percent inhibition is compared to untreated (no oligo) control.

Total $BCL_1$ cellular RNA was isolated using the RNeasy™ kit (Qiagen, Santa Clara Calif.). Northern blotting was performed using standard methods. The cDNA probes were generated from oligonucleotides matching the exon sequences of either exons 2, 8, 9 or 10. Signals were quantitated using a Molecular Dynamics PhosphorImager.

TABLE 1

Nucleotide Sequences of Mouse IL-5R Oligonucleotides-2' MOE gapmers

| ISIS NO. | NUCLEOTIDE SEQUENCE (5' -> 3') | SEQ ID NO: | TARGET SITE[2] | TARGET REGION |
|---|---|---|---|---|
| 18001 | CAAGGACTTCCTTTCCTTTC | 1 | 1288–1307 | Coding/exon 9 |
| 18002 | GCCATTCTACCAAGGACTTC | 2 | 1298–1317 | Coding/exon 9 |
| 18003 | ACAATGAGATGCCATTCTAC | 3 | 1308–1327 | Coding/exon 9 |
| 18004 | TGTTGGGAGCACAATGAGAT | 4 | 1318–1337 | Coding/exon 9 |
| 18005 | AGCAGGCAGCTGTTGGGAGC | 5 | 1328–1347 | Coding/exon 9 |
| 18006 | TGAGAAGATTAACAAGACGA | 6 | 1348–1367 | Coding/exon 9 |
| 18007 | TGCAGATGAGTGAGAAGATT | 7 | 1358–1377 | Coding/exon 9 |

TABLE 1-continued

Nucleotide Sequences of Mouse IL-5R Oligonucleotides-2' MOE gapmers

| ISIS NO. | NUCLEOTIDE SEQUENCE (5' -> 3') | SEQ ID NO: | TARGET SITE[2] | TARGET REGION |
|---|---|---|---|---|
| 18008 | ACTCTGCAGATGAGTGAGAA | 8 | 1362–1381 | Coding/exon 9 |

[1]Emboldened residues, 2'-methoxyethoxy- residues (others are 2'-deoxy-) including "C" residues, 5-methyl-cytosines; all linkages are phosphorothioate linkages.
[2]Nucleotide numbers from Genbank Accession No. D90205, locus name "MUSIL5R,", disclosed herein as SEQ ID NO: 9, to which the oligonucleotide is targeted.

TABLE 2

Effect of 2'-MOE gapmers targeted to murine IL-5 receptorα mRNA exon 9 on membrane and soluble IL-5 receptorα mRNA expression

| ISIS NO. | % inhibition of membrane IL-5 Rα | % inhibition of soluble[1] IL-5 Rα | SEQ ID NO: |
|---|---|---|---|
| 18001 | 35 | 39 | 1 |
| 18002 | 5 | 8 | 2 |
| 18003 | 15 | 20 | 3 |
| 18004 | 10 | 20 | 4 |
| 18005 | 55 | 59 | 5 |
| 18006 | 59 | 65 | 6 |
| 18007 | 65 | 65 | 7 |
| 18008 | 75 | 75 | 8 |

[1]Only one soluble form is detectable by Northern blot in these cells

These gapmers were able to reduce both membrane and soluble forms and each oligonucleotide reduced the two forms approximately equally.

Example 8

Effect of Fully 2'-MOE Oligonucleotidess Targeted to Murine IL-5 Receptorα mRNA Exon 9 on Membrane and Soluble IL-5 Receptorα mRNA Expression Additional oligonucleotides were designed to target exon 9 and intron/exon boundaries; these were uniformly 2'-methoxyethoxy modified with phosphorothioate backbones throughout. These are shown in Table 3 below.

TABLE 3

Nucleotide Sequences of Mouse IL-5R Oligonucleotides- uniform 2' MOE

| ISIS NO. | NUCLEOTIDE SEQUENCE (5' -> 3') | SEQ ID NO: | TARGET SITE | TARGET REGION |
|---|---|---|---|---|
| 21750 | GACTTCCTTTCCTTTCCTGG | 10 | 1284–1303[2] | 18/E9 |
| 21751 | CAAGGACTTCCTTTCCTTTC | 1 | 1288–1307 | 18001 |

TABLE 3-continued

Nucleotide Sequences of Mouse
IL-5R Oligonucleotides-
uniform 2' MOE

| ISIS NO. | NUCLEOTIDE SEQUENCE (5' -> 3') | SEQ ID NO: | TARGET SITE | TARGET REGION |
|---|---|---|---|---|
| 21752 | GCCATTCTACCAAGGACTTC | 2 | 1298–1317 | 18002 |
| 21753 | ACAATGAGATGCCATTCTAC | 3 | 1308–1327 | 18003 |
| 21754 | TGTTGGGAGCACAATGAGAT | 4 | 1318–1337 | 18004 |
| 21755 | AGCAGGCAGCTGTTGGGAGC | 5 | 1328–1347 | 18005 |
| 21756 | AACAAGACGAAGCAGGCAGC | 11 | 1338–1357 | Exon 9 |
| 21757 | TGAGAAGATTAACAAGACGA | 6 | 1348–1367 | 18006 |
| 21758 | TGCAGATGAGTGAGAAGATT | 7 | 1358–1377 | 18007 |
| 21759 | ACTCTGCAGATGAGTGAGAA | 8 | 1362–1381 | 18008 |
| 21760 | CTACACTCTGCAGATGAGTG | 12 | 1366–1383 | E9/E10 |
| 23235 | GCCATTCTATCAAGGACTTC | 13 | mismatch | 21752 |
| 23236 | GCCATGCTATCAAGCACTTC | 14 | " | " |
| 23237 | GCTATCCTATCAAGCACGTC | 15 | " | " |
| 23238 | GACTTCCTTACCTTTCCTGG | 16 | mismatch | 21750 |
| 23239 | GACTTCCTCTTCTTCCCTGG | 17 | " | " |
| 23240 | GACCTCTTTCCCTCTTCTGG | 18 | " | " |

[1]Emboldened residues, 2'-methoxyethoxy- residues (others are 2'-deoxy-) including "C" residues, 5-methyl-cytosines; all linkages are phosphorothioate linkages.
[2]Co-ordinates from Genbank Accession No. D90205, locus name "MUSIL5R" SEQ ID NO: 9.

BCL$_1$ cells were treated with 10 µM of the full-2'-methoxyethyl, full phosphorothioate oligonucleotides for 24 hours and total RNA was extracted and analyzed. Results are shown in Table 4.

TABLE 4

Effect of 2' MOE uniformly modified oligonucleotides targeted to murine IL-5 receptorα mRNA exon on IL-5 mRNA

| ISIS NO. | % control membrane IL-5 Rα | % inhib'n membrane IL-5 Rα | % control soluble IL-5 Rα | % inhib'n soluble IL-5 Rα | SEQ ID NO: |
|---|---|---|---|---|---|
| 21750 | 8 | 92 | 197 | — | 10 |
| 21751 | 9 | 91 | 191 | — | 1 |
| 21752 | 6 | 94 | 194 | — | 2 |
| 21753 | 6 | 94 | 175 | — | 3 |
| 21754 | 8 | 92 | 184 | — | 4 |
| 21755 | 16 | 84 | 181 | — | 5 |
| 21756 | 6 | 94 | 166 | — | 11 |
| 21757 | 19 | 81 | 144 | — | 6 |
| 21758 | 31 | 69 | 116 | — | 7 |
| 21759 | 34 | 66 | 134 | — | 8 |
| 21760 | 55 | 45 | 116 | — | 12 |

[1]Emboldened residues, 2'-methoxyethoxy- residues (others are 2'-deoxy-) including "C" residues, 5-methyl-cytosines; all linkages are phosphorothioate linkages.

All of the fully modified 2'-methoxyethoxy oligonucleotides targeted to murine IL-5 receptorα mRNA exon reduced expression of the membrane form of IL-5 receptorα and increased expression of the soluble form of the receptor. The potencies of these concurrent effects were coordinately diminished as the antisense target site moved toward the 3' end of the exon. The overall amount of IL-5 receptorα transcription is unaffected. This demonstrates that fully 2'-methoxyethoxy-modified oligonucleotides targeted to exon 9 just distal to the intronic 3' splice acceptor site blocked inclusion of exon 9 in the splice product and redirect the splicing machinery to the next downstream splice acceptor site (in intron 9). Reduction of the membrane form of IL-5 receptorα, particularly with no decrease or more particularly with an increase in the soluble form, is believed to have therapeutic utility in diseases associated with IL-5 signal transduction, especially asthma. These results show that splicing has been redirected by use of uniformly 2'-methoxyethoxy oligonucleotides targeted to exon 9 to cause exclusion (skipping) of exon 9 from the spliced mRNA products, resulting in controlled alteration of the ratio of soluble/membrane IL-5 receptor produced.

It was also shown that conversion of an RNAse H-dependent compound (the 2' MOE gapmer ISIS 18002) to an RNAse H-independent compound (the fully- 2' MOE compound 21752) converted this oligonucleotide sequence from an inhibitor of both forms of IL-5 receptorα to one which selectively inhibits the membrane form via splice redirection.

Example 9

Oligonucleotides Targeted to Exon-exon Boundaries of Various Forms of Mouse IL-5 Receptorα mRNA.

Oligonucleotides, either 2' MOE gapmers or uniform 2' MOE, were designed to target exon-exon boundaries of the mature IL-5 receptorα mRNA. The mRNA encoding the membrane form of the receptor has exons 1–11. The mRNA encoding the soluble form of the receptor is missing exon 9 (soluble form 1) or exons 9 and 10 (soluble form 2). In Table 5, the target region designated "E7–E8" indicates that the oligonucleotide is targeted to the exon 7–8 boundary, and so forth.

TABLE 5

Nucleotide Sequences of Mouse IL-5R Oligonucleotides

| ISIS NO. | NUCLEOTIDE SEQUENCE (5' -> 3') | SEQ ID NO: | TARGET SITE[2] | TARGET REGION |
|---|---|---|---|---|
| 21847 | GTTTTTCCTTCTGAATGTGA | 19 | 1139–1158 | E7–E8 |
| 21848 | GTTTTTCCTTCTGAATGTGA | " | | 21847 |
| 21849 | CTTTCCTTTCCCACATAAAT | 20 | 1278–1297 | E8–E9 |
| 21850 | CTTTCCTTTCCCACATAAAT | " | | 21849 |
| 21851 | TAAATGACACACTCTGCAGA | 21 | 1372–1391 | E9–E10 |
| 21852 | TAAATGACACACTCTGCAGA | " | | 21851 |
| 21853 | TAAATGACACCCACATAAAT | 22 | | E8–E10 (soluble form 1) |
| 21854 | TAAATGACACCCACATAAAT | " | | 21853 |
| 21855 | TCGAAGGTTTCCACATAAAT | 23 | | E8–E11 (soluble form 2) |
| 21856 | TCGAAGGTTTCCACATAAAT | " | | 21855 |
| 21969 | CACCTGATTGTGTCTTGTCA | 24 | mismatch | 3'-UTR |
| 21972 | CATCTGCTTCTGTATTGCCA | 25 | | 3'-UTR |
| 22093 | CTACACTCTGCAGATGAGTG | 26 | | 21760 |
| 22094 | GACTTCCTTTCCTTTCCTGG | 27 | | 21750 |
| 23232 | GCCATTCTATCAAGGACTTC | 28 | mismatch | 21752 |

TABLE 5-continued

Nucleotide Sequences of Mouse IL-5R Oligonucleotides

| ISIS NO. | NUCLEOTIDE SEQUENCE (5' -> 3') | SEQ ID NO: | TARGET SITE[2] | TARGET REGION |
|---|---|---|---|---|
| 23233 | GCCATGCTATCAAGCACTTC | 29 | " | " |
| 23234 | GCTATCCTATCAAGCACGTC | 30 | " | " |

[1]Emboldened residues, 2'-methoxyethoxy- residues (others are 2'-deoxy-), all "C" and "C" residues, 5-methyl-cytosines; all linkages are phosphorothioate linkages.
[2]Nucleotide numbers from Genbank Accession No. D90205, locus name "MUSIL5R", SEQ ID NO. 9.

These compounds were tested at 10 μM dose for ability to reduce membrane or soluble IL-5 receptorα mRNA. Results for compounds tested are shown in Table 6.

TABLE 6

Activity of Mouse IL-5R Oligonucleotides against Soluble and Membrane IL-5 receptorα mRNA

| ISIS NO. | SEQ ID NO: | CHEM-ISTRY | % INHIB'N MEMBRANE IL-5 RECEPTOR | % INHIB'N SOLUBLE IL-5 RECEPTOR | TARGET REGION |
|---|---|---|---|---|---|
| 21847 | 19 | uniform 2'-MOE | 23 | 20 | E7–E8 (common) |
| 21848 | " | 2' MOE/ deoxy gapmer | 89 | 86 | 21847 |
| 21849 | 20 | uniform 2'-MOE | 70 | 5 | E8–E9 (membrane) |
| 21850 | " | 2' MOE/ deoxy gapmer | 39 | 25 | 21849 |
| 21851 | 21 | uniform 2'-MOE | 61 | 0 | E9–E10 (membrane) |
| 21852 | " | 2' MOE/ deoxy gapmer | 20 | 14 | 21851 |
| 21853 | 22 | uniform 2'-MOE | 14 | 45 | E8–E10 (soluble form 1) |
| 21854 | " | 2' MOE/ deoxy gapmer | 11 | 14 | 21853 |
| 21855 | 23 | uniform 2'-MOE | 14 | 25 | E8–E11 (soluble form 2) |

As shown in Table 6, selective reduction of expression of the soluble form of IL-5 receptorα could be achieved with antisense oligonucleotides targeted to the exon 8-exon 10 boundary, or, to a lesser extent to the exon 8-exon 11 boundary, both of which junctions are only found in the soluble receptor mRNA. Selective reduction of expression of the membrane form of IL-5 receptors could be achieved with antisense oligonucleotides targeted to the exon 8-exon 9 boundary or exon 9-exon 10 boundary, both of which are only present in the mRNA targeting the membrane form of IL-5 receptorα. Placement of the fully-2' MOE oligonucleotides across the intron/exon boundaries of exon 9 resulted in similar effects as were obtained with fully-modified oligonucleotides positioned inside exon 9.

Example 10

Antisense Oligonucleotides Targeted to Splice Sites in the Human IL-5 Receptorα mRNA mRNA transcripts encoding the membrane form of the human IL-5 receptorα contain exons 1–10 and 12–14. Exon 11 is spliced out. It is, therefore, possible to target sequences in exons 1–10 which are common to both soluble and membrane forms of the receptor, or to selectively target sequences only present in the membrane form (exons 12–14). Oligonucleotides were also designed to target various intron/exon boundaries downstream of exon 11, with the intention of preventing successful splicing out of exon 11 and thus redirecting splice products away from the membrane form and in favor of the soluble form of IL-5 receptorα.

A series of oligonucleotides were designed to target various splice sites or (intron-exon boundaries) in the IL-5 receptor mRNA. These are shown in Table 7 and their effect on IL-5 receptor mRNA and cell surface protein levels is shown in Tables 8 and 9.

TABLE 7

Nucleotide Sequences of Human IL-5R Oligonucleotides

| ISIS NO. | NUCLEOTIDE SEQUENCE (5' -> 3') | SEQ ID NO: | TARGET REGION |
|---|---|---|---|
| 16746 | ACCCAGCTTTCTGCAAAACA | 31 | I13/E14 |
| 16747 | ACCCAGCTTTCTGCAAAACA | 31 | |
| 16748 | ACCCAGCTTTCTGCAAAACA | 31 | |
| 16749 | TCAACATTACCTCATAGTTA | 32 | E13/I13 |
| 16750 | TCAACATTACCTCATAGTTA | 32 | |
| 16751 | TCAACATTACCTCATAGTTA | 32 | |
| 16752 | TAAATGACATCTGAAAACAG | 33 | I12/E13 |
| 16753 | TAAATGACATCTGAAAACAG | 33 | |
| 16754 | TAAATGACATCTGAAAACAG | 33 | |
| 16755 | GAACACTTACATTTTACAGA | 34 | E12/I12 |
| 16756 | GAACACTTACATTTTACAGA | 34 | |
| 16757 | GAACACTTACATTTTACAGA | 34 | |
| 16758 | TCATCATTTCCTGGTGGAAA | 35 | I11/E12 |
| 16759 | TCATCATTTCCTGGTGGAAA | 35 | |
| 16760 | TCATCATTTCCTGGTGGAAA | 35 | |
| 18009 | TCATCATTTACTGGTGGAAA | 36 | mismatch |
| 18010 | TCAGCATTTACTGGTGTAAA | 37 | mismatch |
| 18011 | TCAGCAGTTACTTGTGTAAA | 38 | mismatch |

[1]Emboldened residues, 2'-methoxyethoxy- residues (others are 2'-deoxy-) including "C" residues, 5-methyl-cytosines; all linkages are phosphorothioate linkages.
[2]Target regions refer to intron/exon junctions (splice sites) to which oligonucleotides are targeted. I13/E14 indicates the junction between the 3' end of intron 13 and the 5' end of exon 14. E13/I13 indicates the junction between the 3' end of exon 13 and the 5' end of intron 13. I12/E13 indicates the junction between the 3' end of intron 12 and the 5' end of exon 13.E12/I12 indicates the junction between the 3' end of exon 12 and the 5' end of intron 12. I11/E12 indicates the junction between the 3' end of intron 11 and the 5' end of exon 12. Target sequences are from FIG. 2 of Tuypens, T., et al., Eur. Cytokine Netwe., 1992, 3, 451–459.

TABLE 8

Modulation of Human IL-5 receptorα membrane form mRNA expression by Splice Site Oligonucleotides (18 hr)

| ISIS NO. | SEQ ID NO: | TARGET REGION[2] | % of CONTROL | % INHIB'N |
|---|---|---|---|---|
| 16747 | 31 | I13/E14 | 36% | 64% |
| 16747 | " | | 66 | 34 |
| 16748 | " | | 25 | 75 |
| 16749 | 32 | E13/I13 | 101 | — |
| 16750 | " | | 96 | 4 |
| 16751 | " | | 96 | 4 |
| 16752 | 33 | I12/E13 | 101 | — |
| 16753 | " | | 98 | 2 |

TABLE 8-continued

Modulation of Human IL-5 receptorα membrane form mRNA expression by Splice Site Oligonucleotides (18 hr)

| ISIS NO. | SEQ ID NO: | TARGET REGION[2] | % of CONTROL | % INHIB'N |
|---|---|---|---|---|
| 16754 | " | | 101 | — |
| 16755 | 34 | E12/I12 | 15.5 | 84 |
| 16756 | " | | 96 | 4 |
| 16757 | " | | 91 | 9 |
| 16758 | 35 | I11/E12 | 176 | — |
| 16759 | " | | 81 | 19 |
| 16760 | " | | 76 | 24 |

[1]Emboldened residues, 2'-methoxyethoxy- residues (others are 2'-deoxy-) including "C" residues, 5-methyl-cytosines; all linkages are phosphorothioate linkages.

[2]Target regions refer to intron/exon junctions (splice sites) to which oligonucleotides are targeted. I13/E14 indicates the junction between the 3' end of intron 13 and the 5' end of exon 14. E13/I13 indicates the junction between the 3' end of exon 13 and the 5' end of intron 13. I12/E13 indicates the junction between the 3' end of intron 12 and the 5' end of exon 13. E12/I12 indicates the junction between the 3' end of exon 12 and the 5' end of intron 12. I11/E12 indicates the junction between the 3' end of intron 11 and the 5' end of exon 12.

ISIS 16746, 16748 and 16755 inhibited IL-5 receptor mRNA expression by over 50% and are therefore preferred in this assay. Northern blot analysis indicated that ISIS 16755 inhibited the membrane receptor transcript without significantly inhibiting the soluble form. Thus it is believed that ISIS 16755 redirects splicing in favor of the membrane form, as is consistent with data obtained with other non-RNAse H (e.g., uniform 2'-methoxyethoxy) oligonucleotides targeted to splice sites.

TABLE 9

Modulation of Human IL-5 receptorα protein expression on the Cell Surface by Splice Site Oligonucleotides (36 hr)

| ISIS NO. | NUCLEOTIDE SEQUENCE (5' -> 3') | SEQ ID NO: | TARGET REGION[2] | % of CONTROL | % INHIB |
|---|---|---|---|---|---|
| 16746 | ACCCAGCTTTCTGCAAAACA | 31 | I13/E14 | 35 | 65% |
| 16747 | ACCCAGCTTTCTGCAAAACA | " | " | 80.5 | 19.5 |
| 16748 | ACCCAGCTTTCTGCAAAACA | " | " | 40.5 | 59.5 |
| 16749 | TCAACATTACCTCATAGTTA | 32 | E13/I13 | 75 | 25 |
| 16750 | TCAACATTACCTCATAGTTA | " | " | 91 | 9 |
| 16751 | TCAACATTACCTCATAGTTA | " | " | 101 | — |
| 16752 | TAAATGACATCTGAAAACAG | 33 | I12/E13 | 100.5 | — |
| 16753 | TAAATGACATCTGAAAACAG | " | " | 96 | 4 |
| 16754 | TAAATGACATCTGAAAACAG | " | " | 100.5 | — |
| 16755 | GAACACTTACATTTTACAGA | 34 | E12/I12 | 10.5 | 89.5 |
| 16756 | GAACACTTACATTTTACAGA | " | " | 101 | — |
| 16757 | GAACACTTACATTTTACAGA | " | " | 81 | 19 |
| 16758 | TCATCATTTCCTGGTGGAAA | 35 | I11/E12 | 5.5 | 94.5 |
| 16759 | TCATCATTTCCTGGTGGAAA | " | " | 75.5 | 24.5 |
| 16760 | TCATCATTTCCTGGTGGAAA | " | " | 71 | 29 |

[1]Emboldened residues, 2'-methoxyethoxy- residues (others are 2'-deoxy-) including "C" residues, 5-methyl-cytosines; all linkages are phosphorothioate linkages.

TABLE 9-continued

Modulation of Human IL-5 receptorα protein expression on the Cell Surface by Splice Site Oligonucleotides (36 hr)

[2]Target regions refer to intron/exon junctions (splice sites) to which oligonucleotides are targeted. I13/E14 indicates the junction between the 3' end of intron 13 and the 5' end of exon 14. E13/I13 indicates the junction between the 3' end of exon 13 and the 5' end of intron 13. I12/E13 indicates the junction between the 3' end of intron 12 and the 5' end of exon 13. E12/I12 indicates the junction between the 3' end of exon 12 and the 5' end of intron 12. I11/E12 indicates the junction between the 3' end of intron 11 and the 5' end of exon 12.

ISIS 16746, 16748, 16755 and 16758 inhibited human IL-5 receptorα protein by over 50% in this assay and are therefore preferred. ISIS 16758 and 16755 were chosen for further study. ISIS 16758 was found to have an IC50 of approximately 5 $\mu$M for reduction of IL-5 receptorα cell surface protein in TF-1 cells. A 1-mismatch control had an IC50 of 10 $\mu$M and 3- and 5-mismatch controls did not inhibit IL-5 receptorα expression. ISIS 16758 inhibited IL-5 receptorα protein expression without reducing mRNA levels, consistent with an RNAse H-independent mechanism as predicted for a uniformly 2'-methoxyethoxy modified oligonucleotide.

Example 11

Induction of Apoptosis in TF-1 Cells Treated with IL-5 Receptorα Oligonucleotide $1 \times 10^6$ TF-1 cells cultured in IL-5 (0.5 ng/ml) were collected 48 hours following oligonucleotide treatment (tranfection was by electroporation as described in previous examples) and phosphatidylserine expression was detected as a measure of apoptosis using the Annexin-V staining kit (Clontech, Palo Alto, Calif.) according to the manufacturer's instructions. Briefly, cells were resuspended in 0.2 ml of staining buffer (10 mM Hepes, pH 7.4, 140 mM NaCl, 5 mM $CaCl_2$) and 10 $\mu$M of propidium iodide (50 $\mu$g/ml) and 5 $\mu$l of Annexin V reagent were added at 4° C. for 10 minutes. The samples were diluted with FacsFlow (Becton Dickinson, Franklin Lakes N.J.) buffer and analyzed on a Becton Dickinson FACScan. Results are shown in Table 10 below.

TABLE 10

Apoptosis induction mediated by antisense to human IL-5 receptorα

| ISIS No. | Chemistry | Oligo dose ($\mu$M) | % Apoptotic cells | SEQ ID NO: |
|---|---|---|---|---|
| No oligo | | | 14 | |
| 16758 | Uniform 2'-MOE | 10 | 33.1 | 35 |
| " | | 15 | 40.1 | 35 |
| " | | 20 | 50.4 | 35 |
| 18011 | 5-mismatch for 16758 | 10 | 19 | 38 |
| " | | 15 | 23.6 | 38 |
| " | | 20 | 21.8 | 38 |

Apoptosis was shown to be induced by ISIS 16758.

Example 12

Effect of IL-5 Receptor Oligonucleotides on Cell Proliferation $2.5 \times 10^4$ TF-1 cells were incubated in 96-well plates in 200 µl complete RPMI in the absence of IL-5 for 16 hours following electroporation. IL-5 (0.5 ng/ml) was added and the cultures were pulsed with 1 µCi of [$^3$H]-thymidine for the last 8 hours of a 48-hour culture period. The cells were harvested on glass fiber filters and analyzed for thymidine incorporation (proportional to cell proliferation) by liquid scintillation counting. Results are shown in Table 11. Results are compared to thymidine incorporation in untreated controls.

TABLE 11

Inhibition of IL-5-induced TF-1 cell proliferation by human IL-5 receptorα antisense oligonucleotides

| ISIS No. | Chemistry | Oligo dose (µM) | % of control thymidine incorporation | SEQ ID NO: |
|---|---|---|---|---|
| 16758 | Uniform 2'-MOE | 10 | 42.8 | 35 |
| " | | 15 | 39.2 | " |
| " | | 20 | 19.9 | " |
| 18011 | 5-mismatch for 16758 | 10 | 95.6 | 38 |
| " | | 15 | 97.9 | " |
| " | | 20 | 84.6 | " |

These data demonstrate that ISIS 16758, an antisense inhibitor of IL-5 receptorα, greatly reduces cellular response to IL-5, i.e., cell proliferation in response to IL-5.

Example 13

Antisense Modulation of Splicing in Bcl-x mRNA

Bcl-x is a bcl-2-independent regulator of apoptosis. Boise et al., 1993, Cell 74,597–608. Two isoforms of bcl-x were reported in humans. Bcl-xl (long) contains the highly conserved BH1 and BH2 domains. When transfected into an IL-3 dependent cell line, bcl-xl inhibited apoptosis during growth factor withdrawal, in a manner similar to bcl-2. In contrast, the bcl-x short isoform, bcl-xs, which is produced by alternative splicing and lacks a 63-amino acid region of exon 1 containing the BH1 and BH2 domains, antagonizes the anti-apoptotic effect of either bcl-2 or bcl-xl.

As numbered in Boise et al., Cell, 1993, 608, the bcl-x transcript can be categorized into regions described by those of skill in the art as follows: nucleotides 1–134, 5' untranslated region (5'-UTR); nucleotides 135–137, translation initiation codon (AUG); nucleotides 135–836, coding region, of which 135–509 are the shorter exon 1 of the bcl-xs transcript and 135–698 are the longer exon 1 of the bcl-xl transcript; nucleotides 699–836 are exon 2; nucleotides 834–836, stop codon; nucleotides 837–926, 3' untranslated region (3'-UTR). Between exons 1 and 2 (between nucleotide 698 and 699) an intron is spliced out of the pre-mRNA when the mature bcl-xl (long) mRNA transcript is produced. An alternative splice from position 509 to position 699 produces the bcl-xs (short) mRNA transcript which is 189 nucleotides shorter than the long transcript, encoding a protein product (bcl-xs) which is 63 amino acids shorter than bcl-xl.

The protein of bcl-xL is similar in size and structure to the anti-apoptotic protein bcl-2, and is believed to have a similar anti-apoptotic function, inhibiting cell death upon growth factor withdrawal. In contrast the protein of bcl-xs is believed to inhibit the bcl-2 function, thus promoting programmed cell death (apoptosis).

Example 14

Effect of Antisense Oligonucleotides on Expression of Bcl-xs and Bcl-xl Transcripts In accordance with the present invention, a series of oligonucleotides were designed to target different regions of human bcl-x RNA, using published sequences (Boise, L. H., et al., 1993, Cell 74, 597–608; Genbank Accession No. L20121, locus name "HSBCLXL," incorporated herein as SEQ ID NO: 39). Antisense oligonucleotides were designed to target areas of exon 1 and exon 2 of human bcl-x, particularly around the exon 1/exon 2 splice site and in sequence regions present in bcl-xl but not in bcl-xs. These oligonucleotides are shown in Table 12. All backbone linkage are phosphorothioates; All 2' MOE cytosines are 5-methylcytosines.

TABLE 12

Oligonucleotides targeted to exon1/exon 2 of human bcl-x

| ISIS # | Sequence | Target Region | Target site[2] | SEQ ID NO: |
|---|---|---|---|---|
| 16009 | CTACGCTTTCCACGCACAGT | Exon 1L | 581–600 | 40 |
| 16968 | CTCCGATGTCCCCTCAAAGT | mismatch | 16009 | 41 |
| 15999 | TCCCGGTTGCTCTGAGACAT | AUG | 135–154 | 42 |
| 16972 | TCACGTTGGCGCTTAGCCAT | mismatch | 15999 | 43 |
| 16011 | CTGGATCCAAGGCTCTAGGT | Exon 1L | 664–683 | 44 |
| 22783 | CTGGATCCAAGGCTCTAGGT | Exon 1L | 664–683 | 44 |
| 16012 | CCAGCCGCCGTTCTCCTGGA | Exon 1L 3' end | 679–698 | 45 |
| 22784 | CCAGCCGCCGTTCTCCTGGA | Exon 1L 3' end | 679–698 | 45 |
| 16013 | TAGAGTTCCACAAAAGTATC | Exon 2 5' end | 699–718 | 46 |

TABLE 12-continued

Oligonucleotides targeted to exon1/exon 2 of human bcl-x

| ISIS # | Sequence | Target Region | Target site[2] | SEQ ID NO: |
|---|---|---|---|---|
| 22781 | TAGAGTTCCACAAAAGTATC | Exon 2 5' end | 699–718 | 46 |
| 22782 | CAAAAGTATCCCAGCCGCCG | Exon ½ splice | 689–708 | 47 |
| 22785 | GCCGCCGTTCTCCTGGATCC | Exon 1L | 676–695 | 48 |
| 23172 | GTTCCTGGCCCTTTCGGCTC | Exon 2 | 740–759 | 49 |
| 23173 | CAGGAACCAGCGGTTGAAGC | Exon 2 | 760–779 | 50 |
| 23174 | CCGGCCACAGTCATGCCCGT | Exon 2 | 780–799 | 51 |
| 23175 | TGTAGCCCAGCAGAACCACG | Exon 2 | 800–819 | 52 |

[1]Residues shown in bold are 2'-MOE residues
[2]Co-ordinates from Genbank Accession No. L20121, locus name "HSBCLXL," SEQ ID NO: 39.

Oligonucleotides were evaluated for their respective effects on bcl-xs and bcl-xl mRNA levels in A549 cells along with total bcl-x mRNA levels, using the RIBOQUANT™ RNase protection kit (Pharmingen, San Diego Calif.). All assays were performed according to manufacturer's protocols. Results are shown in Table 13.

showed induction of bcl-xs mRNA after treatment with ISIS 22783 but not the mismatch control ISIS 26080 (CTGGTTACACGACTCCAGGT; SEQ ID NO: 53). ISIS 22783 has also been shown in preliminary experiments to cause slight induction of bcl-xs mRNA expression in vivo in mouse liver.

TABLE 13

Effect of antisense oligonucleotides on bcl-xs and bcl-xl

| ISIS # | SEQ ID NO | % CONTROL bcl-xs | % CONTROL bcl-xl | % CONTROL total bcl-x | bcl-xs/ bcl-xl (%) | bcl-xs/ bcl-xl* |
|---|---|---|---|---|---|---|
| no oligo | — | 100 | 100 | 100 | 17.56 | 1 |
| 16009 | 40 | 20 | 24 | 24 | 12.45 | 0.71 |
| 16968 | 41 | 20 | 15 | 21 | 20.18 | 1.15 |
| 15999 | 42 | ND** | ND | ND | — | — |
| 16972 | 43 | 60 | 91 | 87 | 11.68 | 0.67 |
| 16011 | 44 | ND | ND | ND | — | — |
| 22783 | 44 | 620 | 35 | 120 | 293.1 | 16.69 |
| 16012 | 45 | 48 | 63 | 61 | 13.17 | 0.75 |
| 22784 | 45 | 204 | 72 | 92 | 48.63 | 2.77 |
| 16013 | 46 | 60 | 83 | 82 | 12.46 | 0.71 |
| 22781 | 46 | ND | ND | ND | — | — |
| 22782 | 47 | 64 | 76 | 75 | 15.72 | 0.89 |
| 22785 | 48 | 248 | 53 | 83 | 80.14 | 4.56 |
| 23172 | 49 | 84 | 77 | 79 | 19.38 | 1.1 |
| 23173 | 50 | ND | ND | ND | — | — |
| 23174 | 51 | 56 | 67 | 66 | 14.93 | 0.85 |
| 23175 | 52 | 52 | 82 | 78 | 11.44 | 0.65 |

*In control cells without oligonucleotide, the bcl-xs/bcl-xl mRNA ratio is 17.56. This column gives the change from this number (i.e, where the bcl-xs/bcl-xl mRNA ratio is 17.56, this column reads "1").
**where "ND" is present, the RNA on the gel could not be quantitated.

ISIS 22783, a fully 2'-MOE, full-phosphorothioate oligonucleotide targeted to exon 1 of the bcl-xl transcript (not the bcl-xs transcript), is able to change the ratio of bcl-xs to bcl-xl from 17% to 293%, without reducing the total bcl-x mRNA level in A549 cells. That is, it reduced the bcl-xl form (the anti-apoptotic form of bcl-x) but dramatically increased the bxl-xs form (the pro-apoptotic form). This result is expected to result in promotion of apoptosis.

ISIS 22783 was tested by RNAse protection assay for ability to inhibit bax, another apoptotic gene. It had no effect on bax mRNA levels.

ISIS 22783 is also fully complementary to the murine bcl-x mRNA which makes it useful for animal studies. Treatment of mouse cell lines bEND, AML12 and Hepa all

Example 15

Optimization of 2'-MOE Oligonucleotides Targeting the 5' Splice Site of Bcl-xl

ISIS 22783, the most active oligonucleotide for redirection of splicing, is targeted to a region which is 16–35 nucleotides upstream of the 5' splice site of bcl-xl (at nucleotide 699). A "walk" was done in this region with 20mer 2'-MOE phosphorothioate oligonucleotides targeted to sequences whose 5' ends were 24, 26, 29, 31, 33, 37, 39, 41, 43, 44, 45 and 47 bases upstream of the splice site. These oligonucleotides were screened as before at a dose of 200 nM oligonucleotide for effect on short and long bcl-x transcripts. The oligonucleotides are shown in Table 14 and results are shown in Table 15.

TABLE 14

Optimization of 2' MOE oligonucleotides targeted to bcl-xl 5' splice site region

| ISIS # | Sequence[1] | Target Region | Target site[2] | SEQ ID NO: |
|---|---|---|---|---|
|  | CTCTAGGTGGTCATTCAGGT | Exon 1L | 652–671 | 54 |
|  | GGCTCTAGGTGGTCATTCAG | Exon 1L | 654–673 | 55 |
| 26073 | AGGCTCTAGGTGGTCATTCA | Exon 1L | 655–674 | 56 |
|  | AAGGCTCTAGGTGGTCATTC | Exon 1L | 656–675 | 57 |
|  | CCAAGGCTCTAGGTGGTCAT | Exon 1L | 658–677 | 58 |
| 26066 | ATCCAAGGCTCTAGGTGGTC | Exon 1L | 660–679 | 59 |
| 26067 | GGATCCAAGGCTCTAGGTGG | Exon 1L | 662–681 | 60 |
| 22783 | CTGGATCCAAGGCTCTAGGT | Exon 1L | 664–683 | 44 |
| 26068 | TCCTGGATCCAAGGCTCTAG | Exon 1L | 666–685 | 61 |
| 26069 | TCTCCTGGATCCAAGGCTCT | Exon 1L | 668–687 | 62 |
| 26070 | GTTCTCCTGGATCCAAGGCT | Exon 1L | 670–689 | 63 |
| 26071 | GCCGTTCTCCTGGATCCAAG | Exon 1L | 673–692 | 64 |
| 26072 | CCGCCGTTCTCCTGGATCCA | Exon 1L | 675–694 | 65 |

[1]Residues shown in bold are 2'-MOE residues
[2]Co-ordinates from Genbank locus name "HSBCLXL," Accession No. L20121 (also Z23115), SEQ ID NO:39.

TABLE 15

Optimization of 2' MOE oligonucleotides targeted to bcl-xl 5' splice site region

| ISIS # | SEQ ID NO | % CONTROL bcl-xs | % CONTROL bcl-xl | bcl-xs/bcl-xl |
|---|---|---|---|---|
|  | 54 | 300 | 42 | 7.14 |
|  | 55 | 316 | 47 | 6.72 |
| 26073 | 56 | 374 | 29 | 12.90 |
|  | 57 | 405 | 53 | 7.64 |
|  | 58 | 271 | 26 | 10.42 |
| 26066 | 59 | 400 | 26 | 15.38 |
| 26067 | 60 | 211 | 32 | 6.59 |
| 22783 | 44 | 247 | 47 | 5.25 |
| 26068 | 61 | 166 | 53 | 3.13 |
| 26069 | 62 | 232 | 40 | 5.80 |
| 26070 | 63 | 242 | 37 | 6.54 |
| 26071 | 64 | 295 | 37 | 7.97 |
| 26072 | 65 | 226 | 42 | 5.38 |

As can be seen, all of the oligonucleotides in this region were able to redirect the splice products in favor of bcl-xs. Antisense compounds targeting anywhere in the 47 nucleotides upstream of the 5' splice site (i.e., from nucleotides 652–699 according to the numbering scheme used in Genbank locus name "HSBCLXL," Accession No. L20121 (also Z23115) are therefore preferred. Many of these compounds were even more effective than ISIS 22783 (i.e., gave bcl-xs/xl ratios of greater than 5.25 in this experiment). These compounds are highly preferred.

A dose response can be obtained for oligonucleotide redirection of splice products. This is shown in Table 16. ISIS 26080 is a 5-base mismatch of ISIS 22783.

TABLE 16

Dose Response for oligonucleotide redirection of splice products

| ISIS # | SEQ ID NO: | Oligo Concentration | ratio of bcl-xs/bcl-xl |
|---|---|---|---|
| 26066 | 59 | 50 | 6 |
| " |  | 100 | 11 |
| " |  | 200 | 24 |
| " |  | 400 | 25 |
| " |  | 600 | nd |

TABLE 16-continued

Dose Response for oligonucleotide redirection of splice products

| ISIS # | SEQ ID NO: | Oligo Concentration | ratio of bcl-xs/bcl-xl |
|---|---|---|---|
| 22783 | 44 | 50 | 3 |
| " |  | 100 | 2 |
| " |  | 200 | 7 |
| " |  | 400 | 24 |
| " |  | 600 | 28 |
| 26080 | 53 | 50 | nd |
| " |  | 100 | nd |
| " |  | 200 | <1 |
| " |  | 400 | 1 |
| " |  | 600 | 3 |

It can be demonstrated that ISIS 22783 induces bcl-xs mRNA expression over time in A549 cells with concurrent reduction in bcl-xL mRNA beginning 2–4 hours after treatment with oligoncleotide. The identity of these transcripts was confirmed by nucleotide sequencing.

Example 16

Antisense Sensitization of Cells to UV-induced Cell Death

A549 cells were treated with 100 nM ISIS 22783 or the 5-mismatch ISIS 26080 and exposed to ultraviolet (UV) radiation. The percent apoptotic cells was quantitated by propidium iodide staining according to standard methods. Results are shown in Table 17.

TABLE 17

Combination of ISIS 22783 and UV irradiation

| Compound | UV mJ/M$^2$ | % Apoptotic cells (approx) | SEQ ID NO: |
|---|---|---|---|
| No oligo | 0 | <1 |  |
|  | 50 | 1 |  |
|  | 100 | 10 |  |
|  | 200 | 22 |  |

TABLE 17-continued

Combination of ISIS 22783 and UV irradiation

| Compound | UV mJ/M$^2$ | % Apoptotic cells (approx) | SEQ ID NO: |
|---|---|---|---|
| ISIS 22783 | 0 | 2 | 44 |
|  | 50 | 4 | " |
|  | 100 | 33 | " |
|  | 200 | 27 | " |
| ISIS 26080 | 0 | 1 | 53 |
|  | 50 | 6 | " |
|  | 100 | 15 | " |
|  | 200 | 29 | " |

Thus the behavior of the cells, i.e., response to UV stress, has been changed after antisense treatment resulting in increased apoptosis.

Example 17

Antisense Sensitization of Cells to Cisplatinum-induced Cell Death

A549 cells were treated with 100 nM ISIS 22783 or the 5-mismatch ISIS 26080 and cisplatinum at various doses. The percent apoptotic cells was cells was quantitated by propidium iodide staining according to standard methods. Results are shown in Table 18.

TABLE 18

Combination of ISIS 22783 and Cisplatinum

| Compound | Cisplatinum dose (µg/ml) | % Apoptotic cells (approx) | SEQ ID NO: |
|---|---|---|---|
| No ollgo | 0 | 4 |  |
|  | 1 | 5 |  |
|  | 10 | 8 |  |
|  | 50 | 18 |  |
| ISIS 22783 | 0 | 3 | 44 |
|  | 1 | 6 | " |
|  | 10 | 13 | " |
|  | 50 | 27 | " |
| ISIS 26080 | 0 | 3 | 53 |
|  | 1 | 2 | " |
|  | 10 | 7 | " |
|  | 50 | 21 | " |

Thus the behavior of the cells, i.e., response to cytotoxic chemical stress, has been changed after antisense treatment resulting in increased apoptosis.

Example 18

Antisense Sensitization of Cells to Taxol-induced Cell Death

A549 cells were treated with 100 nM ISIS 22783 or the 5-mismatch ISIS 26080 and taxol at various doses. The percent apoptotic cells was quantitated by propidium iodide staining according to standard methods. Results are shown in Table 19.

TABLE 19

Combination of ISIS 22783 and Taxol

| Compound | Taxol dose (µg/ml) | % Apoptotic cells (approx) | SEQ ID NO: |
|---|---|---|---|
| No oligo | 0 | 2 |  |
|  | 5 | 3 |  |
|  | 10 | 7 |  |
|  | 30 | 16 |  |
| ISIS 22783 | 0 | 8 | 44 |
|  | 5 | 8 | " |
|  | 10 | 15 | " |
|  | 30 | 26 | " |
| ISIS 26080 | 0 | 2 | 53 |
|  | 5 | 3 | " |
|  | 10 | 10 | " |
|  | 30 | 15 | " |

Thus the behavior of the cells, i.e., response to cytotoxic chemical stress, has been changed after antisense treatment resulting in increased apoptosis.

Example 19

Additional Modifications of the ISIS 22783 Sequence

It is believed that modifications in addition to 2'-methoxyethoxy which provide tight binding of the antisense compound to the target and resistance to nucleases are also particularly useful in targeting splice sites. Examples of such modifications include but are not limited to sugar modifications including 2'-dimethylaminooxyethoxy (2'-DMAOE) and 2'-acetamides; backbone modifications such as morpholino, MMI and PNA backbones, and base modifications such as C-5 propyne.

An antisense compound which has the ISIS 22783 sequence and a 2'-DMAOE modification on each sugar was compared to its 2'-MOE analog for ability to alter the ratio of bcl-x splice products. The results are shown in Table 20.

TABLE 20

Comparison of the 2'-MOE and 2'-DMAOE analogs of the ISIS 22783 sequence for effect on bcl-xs/bcl-xl ratio

| Chemistry | SEQ ID NO: | Oligo Concentration | approx. ratio of bcl-xs/bcl-xl |
|---|---|---|---|
| 2'-MOE | 44 | 100 | 4.5 |
|  | " | 200 | 8.5 |
|  | " | 400 | 18 |
| 2'-DMAOE | " | 100 | 1.8 |
|  | " | 200 | 4 |
|  | " | 400 | 12 |

Thus compared to the 2'-MOE compound, the 2'-DMAOE compound showed qualitatively similar, though quantitatively slightly less, ability to alter the ratio of bcl-xs to bcl-xl splice products. 2'-DMAOE compounds are therefore preferred.

Preliminary experiments with a morpholino-backbone compound with the 22783 sequence showed good activity using scrape loading.

What is claimed is:

1. A method of modulation of processing of a selected wild-type cellular mRNA target, said method comprising binding to said target an antisense compound having at least one 2'-methoxyethoxy, 2'-dimethylaminooxyethoxy, 2'-dimethylaminoethoxyethoxy, 2'-acetamide, morpholino, or peptide nucleic acid modification which is specifically hybridizable with said mRNA target and which does not elicit cleavage of the mRNA target upon binding, so that processing of said mRNA target is modulated.

2. The method of claim 1 wherein said modulation of the processing of a selected wild-type cellular mRNA target is modulation of splicing of said mRNA target.

3. The method of claim 1 wherein said antisense compound has a 2'-methoxyethoxy, 2'-dimethylaminooxyethoxy, 2'-dimethylaminoethoxyethoxy or 2'-acetamide modification on substantially every sugar.

4. The method of claim 3 wherein said antisense compound has at least one phosphorothioate backbone linkage.

5. The method of claim 1 wherein said antisense compound is an antisense oligonucleotide.

6. The method of claim 2 wherein said modulation of splicing is a redirection of splicing.

7. The method of claim 2 wherein said modulation of splicing results in an altered ratio of splice products.

8. The method of claim 2 wherein said modulation of splicing results in exclusion of one or more exons from a mature mRNA.

9. The method of claim 8 wherein said antisense compound is targeted to at least a portion of an exon to be excluded.

10. The method of claim 9 wherein said antisense compound is targeted to an intron-exon junction.

11. The method of claim 6 wherein said antisense compound is targeted to at least a portion of a region up to 50 nucleobases upstream from a 5' splice site.

12. The method of claim 11 wherein said redirection of splicing is a decreased frequency of use of said 5' splice site.

13. The method of claim 1 wherein said processing of a selected wild-type cellular mRNA target is polyadenylation of said mRNA target.

14. The method of claim 1 wherein said antisense compound is targeted to a polyadenylation signal or polyadenylation site.

15. The method of claim 1 wherein said processing of a selected wild-type cellular mRNA target is regulating stability of said mRNA target, by targeting said antisense compound to a sequence which controls the stability of said mRNA target.

16. The method of claim 1 wherein said antisense compound which does not elicit cleavage of the mRNA target upon binding contains at least one modification which increases binding affinity for the mRNA target and which increases nuclease resistance of the antisense compound.

17. The method of claim 1 wherein said antisense compound which does not elicit cleavage of the mRNA target upon binding contains at least one nucleoside having a 2' modification of its sugar moiety.

18. The method of claim 17 wherein every nucleoside of said antisense compound has a 2' modification of its sugar moiety.

19. The method of claim 17 wherein said 2' modification is selected from the group consisting of 2'-O-methoxyethyl and 2'-dimethylaminooxyethoxy.

20. The method of claim 1 wherein said antisense compound which does not elicit cleavage of the mRNA target upon binding contains at least one modified backbone linkage other than a phosphorothioate backbone linkage.

21. The method of claim 20 wherein said antisense compound which does not elicit cleavage of the mRNA target upon binding contains a plurality of modified backbone linkages other than phosphorothioate backbone linkages.

22. The method of claim 21 wherein said antisense compound also contains at least one phosphodiester or phosphorothioate backbone linkage.

23. The method of claim 21 wherein said modified backbone linkages alternate with phosphodiester and/or phosphorothioate backbone linkages.

24. The method of claim 20 wherein every backbone linkage is a modified backbone linkage other than a phosphorothioate linkage.

25. The method of claim 20 wherein said modified backbone linkage is a morpholino, peptide nucleic acid or methylene (methylimino) backbone linkage.

26. The method of claim 1 wherein said antisense compound which does not elicit cleavage of the mRNA target upon binding contains at least one modified nucleobase.

27. The method of claim 26 wherein said modified nucleobase is a C-5 propyne.

28. The method of claim 7 wherein said altered ratio of splice products results from an increase or a decrease in the amount of a splice product encoding a membrane form of a protein relative to a soluble form of a protein.

29. The method of claim 28 wherein said protein is a receptor.

30. The method of claim 29 wherein said receptor is a hormone or cytokine receptor.

31. The method of claim 1 wherein said antisense compound has a morpholino or peptide nucleic acid modification at substantially every backbone linkage.

\* \* \* \* \*

SEQUENCE LISTING

<160> NUMBER OF SEQ ID NOS: 65

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 1
caaggacttc ctttcctttc                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 2
gccattctac caaggacttc                                                     20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 3
acaatgagat gccattctac                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 4
tgttgggagc acaatgagat                                                     20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 5
agcaggcagc tgttgggagc                                                     20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 6
tgagaagatt aacaagacga                                                     20

<210> SEQ ID NO 7
<211> LENGTH: 20

<212> TYPE: DNA
<213> ORGANISM: Artificial Sequence
<220> FEATURE:
<223> OTHER INFORMATION: Description of Artificial Sequence:Synthetic

<400> SEQUENCE: 7

```
tgcagatgag tgagaagatt                                                20
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 8

```
actctgcaga tgagtgagaa                                                20
```

<210> SEQ ID NO 9
<211> LENGTH: 3571
<212> TYPE: DNA
<213> ORGANISM: Mus musculus

<400> SEQUENCE: 9

```
gaaataattg gtaaacacag aaaatgtttc aatagaaaaa agaggaaaca gaacactgtg     60
tagccctgtt atcagcagag acagagctaa cgctggggat accaaactag aagaagctca   120
ctggacaggt cccggtatgc agttctattt ttgttgatgg ctctgtatct aatgtgttca   180
tttgtaccaa ggatctaacc agggtcttcc agagtctgag caagcttctc ccactgagct   240
acatcacagc cccctgttta ttggaagaag aaatacttac acctttccag tattcggcta   300
ccatggtgcc tgtgttacta attcttgtgg gagctttggc aacactgcaa gctgacttac   360
ttaatcacaa aaagttttta cttctaccac ctgtcaattt taccattaaa gccactggat   420
tagctcaagt tcttttacac tgggacccaa atcctgacca agagcaaagg catgttgatc   480
tagagtatca cgtgaaaata aatgccccac aagaagacga atatgatacc agaaagactg   540
aaagcaaatg tgtgaccccc cttcatgaag gctttgcagc tagcgtgagg accattctga   600
agagcagcca taactctg gccagcagtt gggtttctgc tgaactcaaa gctccaccag   660
gatctcctgg aacctcggtt acgaatttaa cttgtaccac acacactgtt gtaagtagcc   720
acacccactt aaggccatac caagtgtccc ttcgttgcac ctggcttgtt gggaaggatg   780
cccctgagga cacacagtat ttcctatact acaggtttgg tgttttgact gaaaaatgcc   840
aagaatacag cagagatgca ctgaacagaa atactgcatg ctggtttccc aggacattta   900
tcaacagcaa agggtttgaa cagcttgctg tgcacattaa tggctcaagc aagcgtgctg   960
caatcaagcc ctttgatcag ctgttcagtc cacttgccat tgaccaagtg aatcctccaa  1020
ggaatgtcac agtggaaatt gaaagcaatt ctctctatat acagtgggag aaaccacttt  1080
ctgcctttcc agatcattgc tttaactatg agctgaaaat ttacaacaca aaaaatggtc  1140
acattccaga ggaaaaactg atcgccaata agttcatctc aaaaattgat gatgtttcta  1200
catattccat tcaagtgaga gcagctgtga gctcaccttg cagaatgcca ggaaggtggg  1260
gcgagtggag tcaacctatt tatgtgggaa aggaaggaa gtccttggta gaatggcatc  1320
tcattgtgct cccaacagct gcctgcttcg tcttgttaat cttctcactc atctgcagag  1380
tgtgtcattt atggaccagg ttgtttccac cggttccggc cccaaagagt aacatcaaag  1440
atctccctgt ggttactgaa tatgagaaac cttcgaatga aaccaaaatt gaagttgtac  1500
```

-continued

```
attgtgtgga agaggttgga tttgaagtca tgggaaattc cacgttttga tggcattttg   1560
ccattctgaa atgaactcat acaggactcc gtgataagag caaggactgc tatttcttgg   1620
caaggaggta tttcaaatga acactcagag ccaggcggtg gtagagctcg cctttaatac   1680
cagcacctgg gatgcacaga cgggaggatt tctgagttcg aggccagctt ggtctataaa   1740
gtgagttcca ggacagccag agctacacag agaaaccctg tctcgaaaaa acaaacaaac   1800
aaacaaacaa acaaaaatga acactcaatt tgaatgcaag tcaccaaccc atccagacat   1860
gagtcaccaa tgtcccattt cataaagtgt gcatgcctca ctcaaacctc cttgctcaca   1920
gcatagcacc agactcaccc agagcatggg cctttggttt cctacccaga gtaccatgtt   1980
ataccagtgt gtctttgaaa gttgcttgac ttacctttgaa ctttttgcac aggagacagt   2040
ttttttaagc taatgtcaca catgtttact ttgggttaag ttgccagtgg tagcactcag   2100
ctacagtgac aggaggaaag gatagaactc attgagagtg aacccaaatt caagactgtc   2160
tttcctgacg caagtgggag acacaatttc atggtgcttt tcccctttca gttctagaat   2220
agtttccttt ctagaactgt gcctgtgtct taaagcataa ggtaacattg aggcaaaaac   2280
aaagactatg tcccacatgt ccctgtgttc cataggcctg ttcaaggaaa tgtctaagcc   2340
aaagtaagtt taagtcaccg tgcctggggt gaaaaagatg gttcagatga cgaagaagca   2400
tgagggcctg agattgatca accagcatca agaaacaaca caacaacag cagcagcaac   2460
aacaaaacag tgcaagaagc acattcctat aaccccagag ttgggagata aagacaagag   2520
gatccatggg aattgtagtt caaccagttt agccaattat gttatctcta ggttcactga   2580
gagaaatggt cttaaaaatt taaggtggag agtgactagg cagatcctct gatactgact   2640
tctgccctaa atatgcatac acatgtacac acacaacaca aagacaccat tccctattga   2700
gagagaagac agaagcttgt tcaaggatta aattcttcaa ggcttctagg tactctggaa   2760
atgacctgag aaagacattg aaaataattc tgctttggag gtgattgctg gatctagaat   2820
gtacttccca aagagatgtt gatgaaagag ccttcatggc aacctgttgg tcaactcatg   2880
cttagtcaat tctaatctct taaattaggg tttcctatac atattacaat tgtataaaaa   2940
tgtattctct aaatatcttc attaatgaag ctgtatctat aggtcttttt gatgggctga   3000
acatagaagc aaacacactt atgtgttggg aagaggaata agtagtgata gagggaccta   3060
gtggtagtta ttttacatag tcctgaagag ctaaagacaa tgaaagaaga aatggtactc   3120
acaagagaga gagctatgtc ggggtcctgt cagccaaatc ttgctagtat atgcaatagt   3180
gtctgggttt ggtggttgta tattggatgg ttccctgggt ggggcagtct ctggatggtc   3240
tttccttcca tcacagctct gaaatttgtc tctgtaactc cttccatgag tattttgttc   3300
cccattctaa gaagcagtga agtatccaca cttttggtctt ccttcttctt gagtttcatg   3360
tgttttgcaa attgtgtgcc tggcaataca gaagcagatg ctcacagtca tctattggat   3420
gaaacacagg gcccctaatg aaggagccag agaaagtacc caaggagcta aaagggtctg   3480
caaccctata gcaggaacaa caatatgaac tacccagcaa ccctcagaaa tgtaaatgaa   3540
gaaaatatct aataaaaaaa aaaaaaaaaa a                                  3571
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 10
gacttccttt cctttcctgg                                                    20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 11
aacaagacga agcaggcagc                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 12
ctacactctg cagatgagtg                                                    20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 13
gccattctat caaggacttc                                                    20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 14
gccatgctat caagcacttc                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 15
gctatcctat caagcacgtc                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 16
gacttcctta cctttcctgg                                                    20

<210> SEQ ID NO 17
<211> LENGTH: 20
<212> TYPE: DNA

```
<213> ORGANISM: Artificial Sequence
<220> FEATURE:
<223> OTHER INFORMATION: Description of Artificial Sequence:Synthetic

<400> SEQUENCE: 17
gacttcctct tcttccctgg                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 18
gacctctttc cctcttctgg                                                    20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 19
gttttccctt ctgaatgtga                                                    20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 20
ctttcctttc ccacataaat                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 21
taaatgacac actctgcaga                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 22
taaatgacac ccacataaat                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 23
tcgaaggttt ccacataaat                                                    20
```

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 24
cacctgattg tgtcttgtca                                         20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 25
catctgcttc tgtattgcca                                         20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 26
ctacactctg cagatgagtg                                         20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 27
gacttccttt cctttcctgg                                         20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 28
gccattctat caaggacttc                                         20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 29
gccatgctat caagcacttc                                         20

<210> SEQ ID NO 30
<211> LENGTH: 20
<212> TYPE: DNA
<213> ORGANISM: Artificial Sequence
<220> FEATURE:

```
<223> OTHER INFORMATION: Description of Artificial Sequence:Synthetic

<400> SEQUENCE: 30
gctatcctat caagcacgtc                                               20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 31
acccagcttt ctgcaaaaca                                               20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 32
tcaacattac ctcatagtta                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 33
taaatgacat ctgaaaacag                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 34
gaacacttac attttacaga                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 35
tcatcatttc ctggtggaaa                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 36
tcatcattta ctggtggaaa                                               20
```

```
<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 37
tcagcattta ctggtgtaaa                                                    20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 38
tcagcagtta cttgtgtaaa                                                    20

<210> SEQ ID NO 39
<211> LENGTH: 926
<212> TYPE: DNA
<213> ORGANISM: Homo sapiens

<400> SEQUENCE: 39
gaatctcttt ctctcccttc agaatcttat cttggctttg gatcttagaa gagaatcact        60
aaccagagac gagactcagt gagtgagcag gtgttttgga caatggactg gttgagccca       120
tccctattat aaaaatgtct cagagcaacc gggagctggt ggttgacttt ctctcctaca       180
agctttccca gaaaggatac agctggagtc agtttagtga tgtggaagag aacaggactg       240
aggccccaga agggactgaa tcggagatgg agaccccag tgccatcaat ggcaacccat        300
cctggcacct ggcagacagc cccgcggtga atggagccac tgcgcacagc agcagtttgg       360
atgcccggga ggtgatcccc atggcagcag taaagcaagc gctgagggag gcaggcgacg       420
agtttgaact gcggtaccgg cgggcattca gtgacctgac atcccagctc cacatcaccc       480
cagggacagc atatcagagc tttgaacagg tagtgaatga actcttccgg gatgggggtaa      540 actgggttcg cattgtggcc ttttctcct tcggcggggc actgtgcgtg gaaagcgtag       600
acaaggagat gcaggtattg gtgagtcgga tcgcagcttg gatggccact tacctgaatg       660
accacctaga gccttggatc caggagaacg gcggctggga tactttttgtg gaactctatg     720 ggaacaatgc agcagccgag agccgaaagg gccaggaacg cttcaaccgc tggttcctga      780
cgggcatgac tgtggccggc gtggttctgc tgggctcact cttcagtcgg aaatgaccag      840
acactgacca tccactctac cctcccaccc ccttctctgc tccaccacat cctccgtcca      900
gccgccattg ccaccaggag aacccg                                           926

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 40
ctacgctttc cacgcacagt                                                    20

<210> SEQ ID NO 41
<211> LENGTH: 20
<212> TYPE: DNA
```

```
<213> ORGANISM: Artificial Sequence
<220> FEATURE:
<223> OTHER INFORMATION: Description of Artificial Sequence:Synthetic

<400> SEQUENCE: 41
ctccgatgtc ccctcaaagt                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 42
tcccggttgc tctgagacat                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 43
tcacgttggc gcttagccat                                                    20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 44
ctggatccaa ggctctaggt                                                    20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 45
ccagccgccg ttctcctgga                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 46
tagagttcca caaaagtatc                                                    20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 47
caaaagtatc ccagccgccg                                                    20
```

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 48
gccgccgttc tcctggatcc                                          20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 49
gttcctggcc ctttcggctc                                          20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 50
caggaaccag cggttgaagc                                          20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 51
ccggccacag tcatgcccgt                                          20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 52
tgtagcccag cagaaccacg                                          20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 53
ctggttacac gactccaggt                                          20

<210> SEQ ID NO 54
<211> LENGTH: 20
<212> TYPE: DNA
<213> ORGANISM: Artificial Sequence
<220> FEATURE:

<223> OTHER INFORMATION: Description of Artificial Sequence:Synthetic

<400> SEQUENCE: 54
ctctaggtgg tcattcaggt 20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 55
ggctctaggt ggtcattcag 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 56
aggctctagg tggtcattca 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 57
aaggctctag gtggtcattc 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 58
ccaaggctct aggtggtcat 20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 59
atccaaggct ctaggtggtc 20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 60
ggatccaagg ctctaggtgg 20

```
<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 61
tcctggatcc aaggctctag                                                    20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 62
tctcctggat ccaaggctct                                                    20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 63
gttctcctgg atccaaggct                                                    20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 64
gccgttctcc tggatccaag                                                    20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 65
ccgccgttct cctggatcca                                                    20
```